(12) United States Patent
Azizian

(10) Patent No.: US 10,729,506 B2
(45) Date of Patent: Aug. 4, 2020

(54) SYSTEM AND METHOD FOR VIRTUAL FEEDBACK WITH HAPTIC DEVICES

(71) Applicant: INTUITIVE SURGICAL OPERATIONS, INC., Sunnyvale, CA (US)

(72) Inventor: Mahdi Azizian, Santa Clara, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 24 days.

(21) Appl. No.: 16/261,122

(22) Filed: Jan. 29, 2019

(65) Prior Publication Data

US 2019/0151039 A1 May 23, 2019

Related U.S. Application Data

(63) Continuation of application No. 15/128,397, filed as application No. PCT/US2015/021662 on Mar. 20, 2015, now Pat. No. 10,251,719.

(Continued)

(51) Int. Cl.
*A61B 34/00* (2016.01)
*G06F 3/01* (2006.01)
*A61B 18/00* (2006.01)

(52) U.S. Cl.
CPC .............. *A61B 34/76* (2016.02); *A61B 34/72* (2016.02); *G06F 3/016* (2013.01); *A61B 2018/00297* (2013.01); *A61B 2034/742* (2016.02)

(58) Field of Classification Search
None
See application file for complete search history.

(56) References Cited

U.S. PATENT DOCUMENTS 5,459,382 A * 10/1995 Jacobus ................. B25J 9/1689
318/568.1
5,631,861 A * 5/1997 Kramer .................... G06F 3/011
414/5

(Continued)

FOREIGN PATENT DOCUMENTS

WO WO-9914842 A1 3/1999
WO WO-2008054856 A2 5/2008

OTHER PUBLICATIONS

Extended European Search Report for Application No. EP15768155, dated Nov. 22, 2017, 8 pages.

(Continued)

*Primary Examiner* — Ramesh B Patel
(74) *Attorney, Agent, or Firm* — Artegis Law Group, LLP

(57) ABSTRACT

Systems and methods of virtual feedback include a virtual feedback device virtually coupled between a first and second device and a control unit. The control unit is configured to select a virtual feedback model (VFM) for the virtual feedback device from among a plurality of VFMs; configure the VFM; determine, based on information from one or more first sensors for detecting information related to a position of the first device and one or more second sensors for detecting information related to a position of the second device, a relative displacement between the first second devices; determine, based on the relative displacement and the VFM, a feedback level; send feedback commands, based on the feedback level, to one or more first actuators for inducing feedback on the first device and to one or more second actuators for inducing feedback on the second device.

20 Claims, 6 Drawing Sheets

Related U.S. Application Data

(60) Provisional application No. 61/969,686, filed on Mar. 24, 2014.

(56) References Cited

U.S. PATENT DOCUMENTS

| | | | | |
|---|---|---|---|---|
| 6,059,506 | A * | 5/2000 | Kramer | G06F 3/011 414/5 |
| 6,421,048 | B1 * | 7/2002 | Shih | G06F 3/016 345/419 |
| 6,437,771 | B1 * | 8/2002 | Rosenberg | A63F 13/06 345/156 |
| 7,747,311 | B2 * | 6/2010 | Quaid, III | A61B 17/3403 600/424 |
| 8,641,663 | B2 * | 2/2014 | Kirschenman | A61B 17/2909 604/95.01 |
| 9,993,222 | B2 * | 6/2018 | Azizian | A61B 6/547 |
| 2001/0043847 | A1 * | 11/2001 | Kramer | G06F 3/014 414/5 |
| 2001/0045941 | A1 * | 11/2001 | Rosenberg | A63F 13/06 345/161 |
| 2003/0210259 | A1 * | 11/2003 | Liu | G06F 3/016 715/702 |
| 2004/0106916 | A1 * | 6/2004 | Quaid | A61B 34/76 606/1 |
| 2004/0254771 | A1 * | 12/2004 | Riener | G09B 23/32 703/7 |
| 2007/0282228 | A1 * | 12/2007 | Einav | A61B 5/16 601/33 |
| 2009/0184923 | A1 * | 7/2009 | Schena | G06F 3/03543 345/156 |
| 2009/0326556 | A1 * | 12/2009 | Diolaiti | A61B 1/00009 606/130 |
| 2010/0234857 | A1 * | 9/2010 | Itkowitz | A61B 34/77 606/130 |
| 2011/0014596 | A1 * | 1/2011 | Kurenov | G09B 23/285 434/262 |
| 2011/0032090 | A1 * | 2/2011 | Provancher | G06F 3/039 340/407.1 |
| 2011/0218774 | A1 * | 9/2011 | Ikits | G06F 3/016 703/1 |
| 2012/0109150 | A1 * | 5/2012 | Quaid | A61N 1/3605 606/130 |
| 2015/0051519 | A1 * | 2/2015 | Morbi | A61G 7/1059 601/26 |
| 2015/0157416 | A1 * | 6/2015 | Andersson | A61B 34/20 606/102 |
| 2016/0345929 | A1 * | 12/2016 | Azizian | G05B 19/4061 |
| 2017/0172681 | A1 | 6/2017 | Azizian | |
| 2018/0235565 | A1 * | 8/2018 | Azizian | A61B 6/547 |

OTHER PUBLICATIONS

International Search Report and Written Opinion for Application No. PCT/US15/21662, dated Jun. 10, 2015, 29 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

SYSTEM AND METHOD FOR VIRTUAL FEEDBACK WITH HAPTIC DEVICES

RELATED APPLICATIONS

The present application is a continuation of U.S. patent application Ser. No. 15/128,397 filed Sep. 22, 2016, which is the U.S. national phase of International Application No. PCT/US2015/021662 filed Mar. 20, 2015, which designated the U.S. and claims priority to U.S. Provisional Patent Application No. 61/969,686 entitled "System and Method for Virtual Feedback with Haptic Devices" filed Mar. 24, 2014, the entire contents of each of which are herein incorporated by reference.

TECHNICAL FIELD

The present disclosure relates generally to haptic devices for computing systems and more particularly to the use of virtual feedback with haptic devices.

BACKGROUND

More and more devices are being replaced with electronic and electro-mechanical devices of ever increasing complexity. This is especially true in the hospitals of today with large arrays of autonomous and semiautonomous electronic devices being found in operating rooms, interventional suites, intensive care wards, emergency rooms, and the like. For example, glass and mercury thermometers are being replaced with electronic thermometers, intravenous drip lines now include electronic monitors and flow regulators, and traditional hand-held surgical instruments are being replaced by computer-assisted medical devices.

A common improvement in many of these devices is the replacement of largely mechanical device controls with hybrid electro-mechanical controls that provide drive-by-wire functionality. Rather than rely on an arrangement of mechanical parts including linkages, pivots, springs, and/or the like, these hybrid electro-mechanical controls monitor an input mechanism, such as a dial, joy stick, switch, articulated arm, and/or the like, to receive commands from an operator. Changes in the input device are converted to input electrical signals that are passed to a control system for processing. The processed input electrical signals are used to determine output electrical signals that become control signals for one or more corresponding actuators. In this way, the operator controls the behavior of the electro-mechanical device indirectly through the processing performed by the control system.

This approach allows for added flexibility in how the electro-mechanical device can be operated. Not only can the parameters and/or algorithms of the control system be adjusted to change the behavior of the electro-mechanical device, but the lesser reliance on potentially complex linkages, pivots, and springs may result in simpler mechanical designs, smaller devices, and/or the like. In addition, the use of electro-mechanical controls may reduce the amount of force that an operator may exert to obtain a corresponding operation of the electro-mechanical device. Further, the use of haptic input devices allows the control system to additionally provide force feedback to the operator along with the control signals for the actuators.

Accordingly, it is desirable to provide improved methods and systems for providing feedback to operators through haptic input devices.

SUMMARY

Consistent with some embodiments, a control unit for a computer-assisted medical device includes one or more processors and an interface coupling the control unit to a first input device. The control unit is configured to determine a reference point for the first input device, select a first virtual feedback model (VFM) for the first input device from among a plurality of VFMs for the first input device, configure one or more parameters of the first VFM, determine a first position of the first input device based on information from one or more first sensors associated with the first input device, determine a first feedback level for the first input device based on the reference point, the first position, and the first VFM, and send one or more first feedback commands to one or more first actuators associated with the first input device based on the first feedback level.

Consistent with some embodiments, a method of providing feedback on an input device of a computer-assisted medical device includes determining a reference point for the input device, selecting a first VFM for the input device from among a plurality of VFMs for the input device, configuring one or more parameters of the first VFM, determining a position of the input device based on information from one or more sensors associated with the input device, determining a feedback level for the input device based on the reference point, the position, and the first VFM, and sending one or more feedback commands to one or more actuators associated with the input device based on the feedback level.

Consistent with some embodiments, a haptic input device for use with a computer-assisted medical device includes an input control, one or more sensors for detecting information related to a position of the input control, one or more actuators for inducing feedback on the input control, a virtual feedback device virtually coupled to the input control, and a control unit. The control unit includes one or more processors and an interface coupling the control unit to the input control. The control unit is configured to determine a reference point for the input control, select a first VFM for the virtual feedback device, configure the first VFM, determine the position of the input control based on information received from the one or more sensors, determine a feedback level for the input control based on the reference point, the position, and the first VFM, and send one or more feedback commands to the one or more actuators based on the feedback level.

Consistent with some embodiments, a compliant motion system for use with a computer-assisted medical device includes a first device, one or more first sensors for detecting information related to a position of the first device, one or more first actuators for inducing feedback on the first device, one or more second sensors for detecting information related to a position of the second device, one or more second actuators for inducing feedback on the second device, a virtual feedback device virtually coupled between the first device and the second device, and a control unit. The control unit includes one or more processors and an interface coupling the control unit to the first device and the second device. The control unit is configured to select a first VFM for the virtual feedback device from among a plurality of VFMs for the virtual feedback device, configure the first VFM, determine a relative position between the first device and the second device based on information received from the one or more first sensors and the one or more second sensors, determine a feedback level based on the relative position and the first VFM, send one or more first feedback commands to the one or more first actuators based on the feedback level, and send one or more second feedback commands to the one or more second actuators based on the feedback level.

Consistent with some embodiments, a method of operating a computer-assisted medical device. The method includes sending feedback determined according to a first virtual feedback model (VFM) for a haptic control input, receiving a command to configure the haptic input control according to a second VFM for the haptic input control, and sending, to the haptic control input, feedback determined according to a second VFM. The feedback determined according the first and second VFMs is sent to the haptic control input.

In the figures, elements having the same designations have the same or similar functions.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Figure 1A:
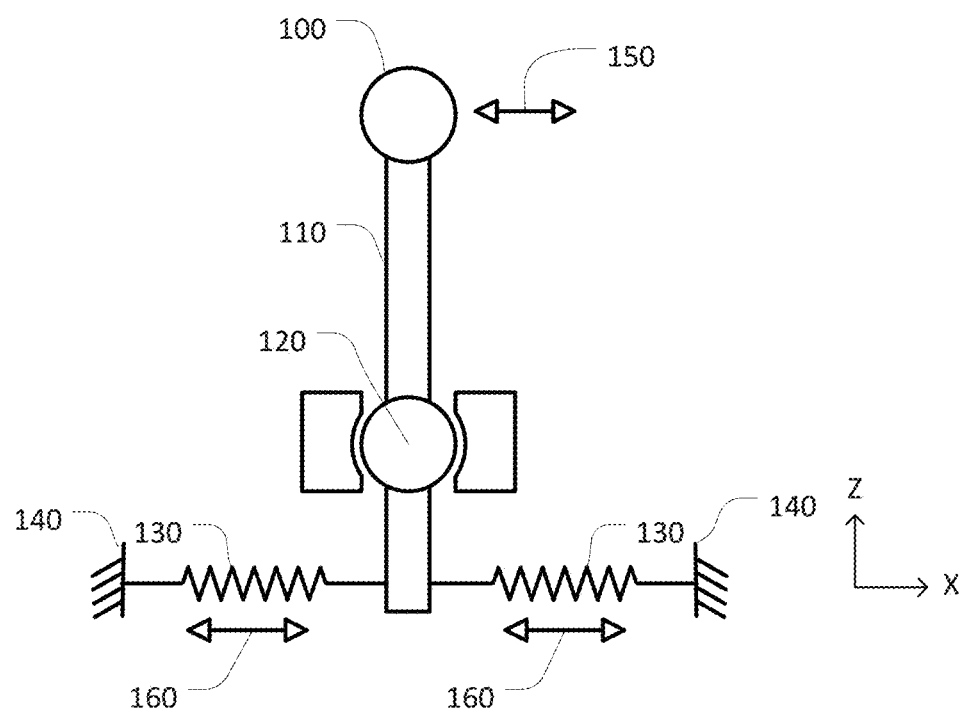
FIGS. 1A and 1B are simplified diagrams of a mechanical input device having force feedback.
Figure 1B:
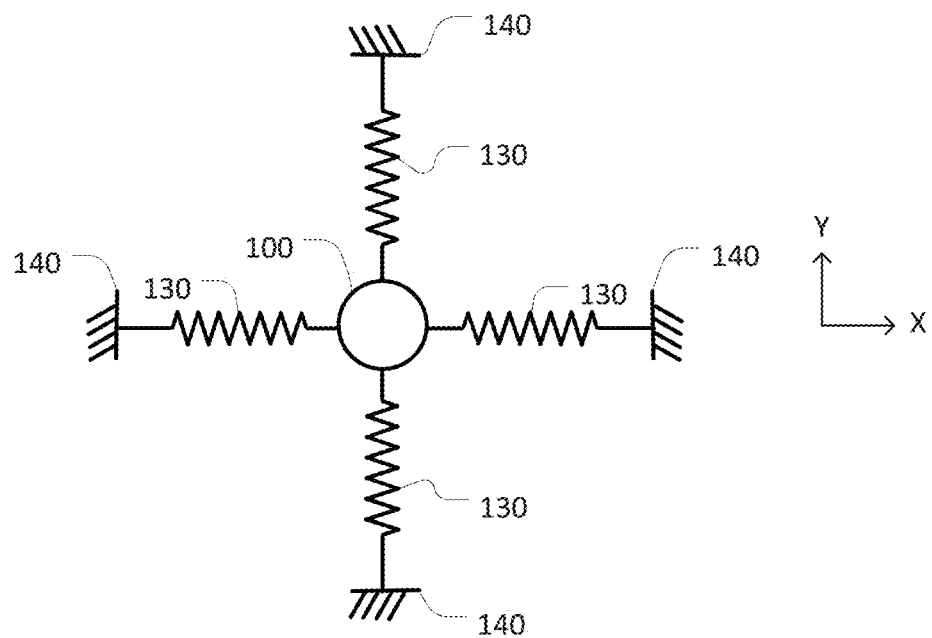

FIGS. 1A and 1B are simplified diagrams of a side-view and a top-view, respectively, of a mechanical input device 100. For example, the mechanical input device 100 may be consistent with a joy stick. Mechanical input device 100 includes an arrangement of mechanical parts that may be used to control another device or system. Mechanical input device 100 includes a shaft 110 and a pivoting mechanism 120. As shown in FIG. 1A, an operator of mechanical input device 100 may manipulate an upper end of shaft 110. As the operator manipulates the upper end of shaft 110, the motion rotates shaft 110 about pivoting mechanism 120. At a lower end of shaft 110, one or more springs 130 are coupled between shaft 110 and respective anchor points 140. As lateral force is applied to the upper end of shaft 110 in the directions of arrows 150 (i.e., the x-direction), the upper end of the shaft 110 is displaced laterally causing shaft 110 to rotate about pivoting mechanism 120. This rotation then results in a corresponding lateral displacement of the lower end of shaft 110, which results in the stretching and/or compressing of the springs 130 in the directions of arrows 160. For example, when the lateral displacement of the upper end of shaft 110 is toward the left as shown in FIG. 1A, the lateral displacement of the lower end of shaft 110 is to the right causing the left spring 130 to stretch and the right spring 130 to compress. As the left spring 130 stretches, it may generate a force that pulls the lower end of shaft 110 to the left, and as the right spring 130 compresses, it may generate a force that pushes the lower end of shaft 110 to the left. When the lateral displacement of the upper end of shaft 110 is to the right, the opposite may occur. Thus, both the left and right spring 130 may operate to push shaft 110 back to an equilibrium position or a reference point. In some examples, this tendency to return to equilibrium may be used to resist lateral displacement of the upper end of shaft 110, provide force and/or haptic feedback to the operator, and/or to provide a dead-man's mechanism that returns mechanical input device 100 to the equilibrium position/reference point in the absence of lateral force from the operator.

The top view of FIG. 1B shows that additional springs 130 and anchor points 140 may be used to provide return to equilibrium forces in more than one direction. The four springs 130 of FIG. 1B may be used to provide resistive and/or feedback force to the operator of mechanical input device 100 to displacements of shaft 110 in any lateral direction. The left and right springs 130 in FIG. 1B may provide feedback force to x-direction displacements and the top and bottom spring 130 in FIG. 1B may provide feedback force to y-direction displacements. In combination, the x-direction and y-direction feedback forces provide feedback force to displacements in any combination of the x- and y-directions and help create an equilibrium position/reference point for shaft 110 in the x- and y-directions.

Although not shown in FIG. 1, mechanical input device 100 may provide commands to a mechanical and/or an electro-mechanical control system. In some examples, shaft 110 may be used to activate one or more switches in response to the lateral displacements of the operator. In some examples, pivoting mechanism 120 may include one or more position sensors for determining angular displacement of shaft 120 from its equilibrium or reference orientation. In some examples, the rotational sensor may be implemented using a potentiometer, an optical encoder, Hall Effect sensor, and/or the like. In some examples, one or more of springs 130 may be coupled to displacement and/or force sensors to determine the magnitude by which each of springs 130 is being stretched and/or compressed. In some examples, the force sensors may include strain gauges, and/or the like.

Mechanical input device 100 demonstrates some of the limitations of mechanical input systems. In some embodiments it may not be possible to change either the force feedback characteristics or the reference point without physically making changes to mechanical input device 100. In some examples, changing the force feedback characteristics may involve replacing one or more of the springs 130 with springs having a different stiffness or spring constant and/or adjusting the location of pivoting mechanism 120 between the upper and lower ends of shaft 110. In some examples, changing the reference point may involve using longer or shorter springs 130, changing the positions of anchor points 140 relative to shaft 110, and/or the like.

In some embodiments, it may not be possible to easily provide different kinds of force feedback to the operator. As designed, mechanical input device 100 provides a force resisting the operator as the operator introduces lateral displacement to the upper end of shaft 110. In some examples, it may not be possible to easily adapt mechanical input device 100 to oppose or resist movement in the z-direction and/or rotations of shaft 110 about its longitudinal axis. In some examples, as more complex springs and/or other mechanical dampers are added to mechanical input device 100, the complexity and the amount of space occupied by mechanical input device 100 may become impractical and/or unacceptable.

Figure 2:
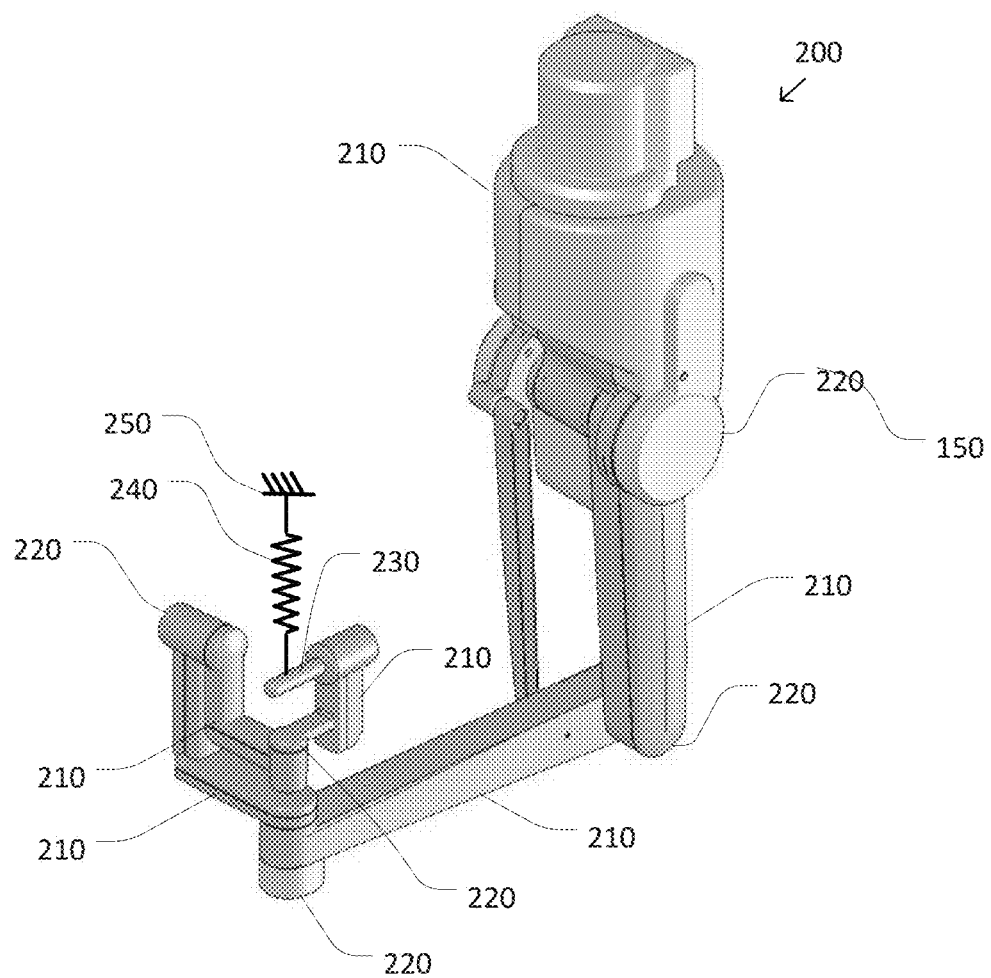
FIG. 2 is a simplified diagram of an articulated input control according to some embodiments.

FIG. 2 is a simplified diagram of an articulated input control 200 according to some embodiments. The articulated input control 200 of FIG. 2 further demonstrates the limitations of mechanical feedback elements in the context of an input device having more than the two degrees of freedom of mechanical input device 100. As shown in FIG. 2, articulated input control 200 includes a series of links 210 and joints 220 that form an articulated arm that has a handle 230 located at its distal end. In some examples, handle 230 is designed to be manipulated by an operator who may change both the position and the orientation of handle 230 during use of articulated input control 200. In some examples, the links 210 and joints 220 of articulated input control 200 may allow manipulation of handle 230 through six degrees of freedom (e.g., x, y, and z positions as well as roll, pitch, and yaw orientations) within limits imposed by ranges of motion limits on joints 220 and the sizes and shapes of links 210. In some embodiments, articulated input control 200 may correspond to a master input control found in a da Vinci® Surgical System commercialized by Intuitive Surgical, Inc. of Sunnyvale, Calif.

To illustrate some of the problems in providing force feedback and/or return to reference point behavior to handle 230, a feedback mechanism 240 is shown coupled between handle 230 and an anchor point 250. Because of the large flexibility in motion of handle 230 due to the links 210 and joints 220, it is likely that implementation of feedback mechanism 240 and anchor point 250 as physical components will result in feedback mechanism 240 and/or anchor point 250 to interfere with the ranges of motion for links 210 and joints 220. This is especially true when the reference point for handle 230 is defined in a world coordinate system and not in a coordinate system that is relative to handle 230. As feedback forces are desired for additional degrees of freedom, any increase in the number of physical feedback mechanisms and/or anchor points is likely to further compound the interference problem. Additionally, as additional physical feedback mechanisms and/or anchor points are added for the additional degrees of freedom, the mechanical complexity of the resulting system may become quite high. As a further problem, designing the physical feedback mechanisms and/or anchor points to allow changes in the location of the reference point and/or the amount of feedback force for different displacements may not be easy and/or practical.

Consequently, for systems that have input devices that would like to take advantage of movable reference points and/or adjustable feedback forces, physical feedback mechanisms are generally not recommended. This is especially true for input devices with large numbers of degrees of freedom, such as articulated input control 200. To provide flexibility in reference point locations and feedback force levels, one solution is to use virtual feedback mechanisms with haptic input devices. For example, for articulated input control 200 in FIG. 2, feedback mechanism 240 may be implemented as a virtual feedback mechanism and anchor point 250 may be implemented as a virtual anchor point.

Figure 3:
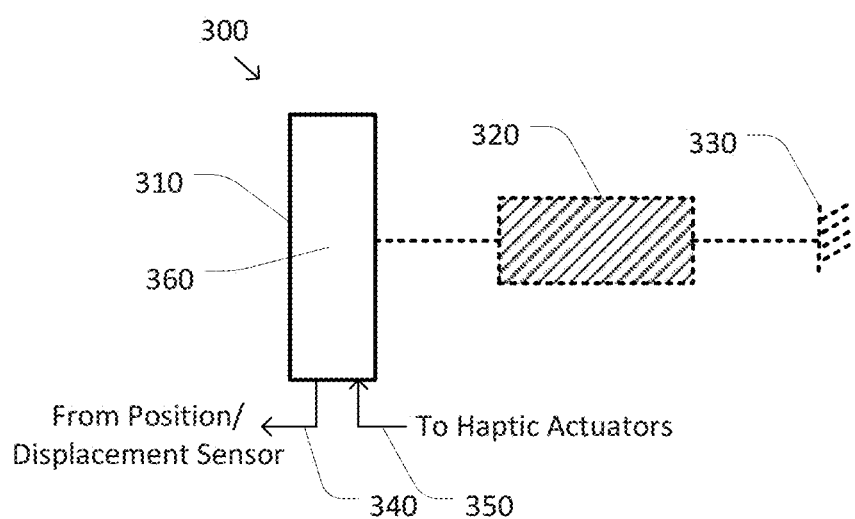
FIG. 3 is a simplified diagram of an input device with a virtual feedback mechanism according to some embodiments.

FIG. 3 is a simplified diagram of an input device 300 with a virtual feedback mechanism according to some embodiments. As shown in FIG. 3, input device 300 includes an input control 310. Input control 310 is capable of being moved by an operator in at least a horizontal direction consistent with a slider or similar input control so that input control 310 may be moved at least to the left or right as shown in FIG. 3.

Although not completely shown in FIG. 3, input device 300 and/or input control 310 may be coupled to one or more sensors that may detect the position and/or the changes in position of input control 310. In some examples, each of the one or more sensors may include potentiometers, optical encoders, Hall Effect sensors, and/or the like. In some examples, the one or more sensors may generate an electrical signal encoding the position of input control 310 and/or indications of movement of input control 310 and then output those values as one or more electrical signals on one or more outputs 340. In some embodiments, input control 310 may be a haptic control including one or more actuators or other mechanisms that may apply feedback to input control 310. As the amount of feedback to apply to input control 310 is determined, it may be communicated to input control 310 using one or more electrical signals on one or more inputs 350. The electrical signals on the one or more outputs 340 and/or the one or more inputs 350 may use any suitable signaling pattern or technique including analog voltages or currents, one or more pulses or pulse patterns, pulse width modulation, one or more command bits or bytes, network packets, and/or the like.

Rather than constrain input control 310 with a mechanical feedback mechanism, such as one of the springs 130, input control 310 is virtually coupled to a virtual feedback mechanism 320 which may be anchored to a virtual anchor point 330. In some examples, input control 310 may be consistent with handle 230, virtual feedback mechanism 320 may be consistent with feedback mechanism 240, and virtual anchor point 330 may be consistent with anchor point 250. As input control 310 is moved, the position and/or the changes in position of input control 310 are applied to a virtual feedback model associated with virtual feedback mechanism 320. The virtual feedback model may then be used to determine the amount, if any, of feedback to be applied to input control 310 via the one or more haptic actuators.

In some embodiments, the virtual feedback model of virtual feedback mechanism 320 may be consistent with that of a virtual spring. As input control 310 moves left and right, the movement may be interpreted as a displacement from a reference point 360 associated with input control 310. As the displacement increases and/or decreases, this may be interpreted as stretching and/or compressing of the virtual spring. By assigning a virtual spring constant to the virtual spring, the displacements may be converted to one or more force or other values that may be communicated back to the one or more haptic actuators.

Because virtual feedback mechanism 320 is virtual, its use in generating feedback for input control 310 is very flexible, depending upon the virtual feedback model used with virtual feedback mechanism 320 and the functional limits of the one or more haptic actuators. As long as the position, displacement, changes in position, and/or changes in displacement of input control 310 are made available to the virtual feedback model, any mapping may be used to convert the position, displacement, changes in position, and/or changes in displacement into corresponding feedback. The advantages of such an approach include the ability to easily change the magnitude and/or profile of the mapping used in the virtual feedback model and/or to change the position of input control 310 that corresponds to reference point 360.

In some embodiments, the virtual feedback model of virtual feedback mechanism 320 may be configured so as to model any desired feedback behavior. In some examples, virtual feedback mechanism 320 may emulate a mechanical feedback device even though the space around input control 310 may not be capable of supporting such a mechanical feedback device. In some examples, the emulated mechanical feedback device may include a mechanical spring, a damper, a dashpot, a shock absorber, a gas spring, and/or the like. In some examples, virtual feedback mechanism 320 and the virtual feedback model may emulate feedback that may not be practical and/or even possible to implement using mechanical feedback devices. For example, this may include a virtual spring of zero size that opposes any displacement about a reference point. In some examples, because physical size is irrelevant to virtual feedback mechanism 320, the location of virtual anchor point 330 may correspond to reference point 360. In some examples, the relative positions between virtual anchor point 330 and reference point 360 may depend on the virtual feedback model.

Figure 4:
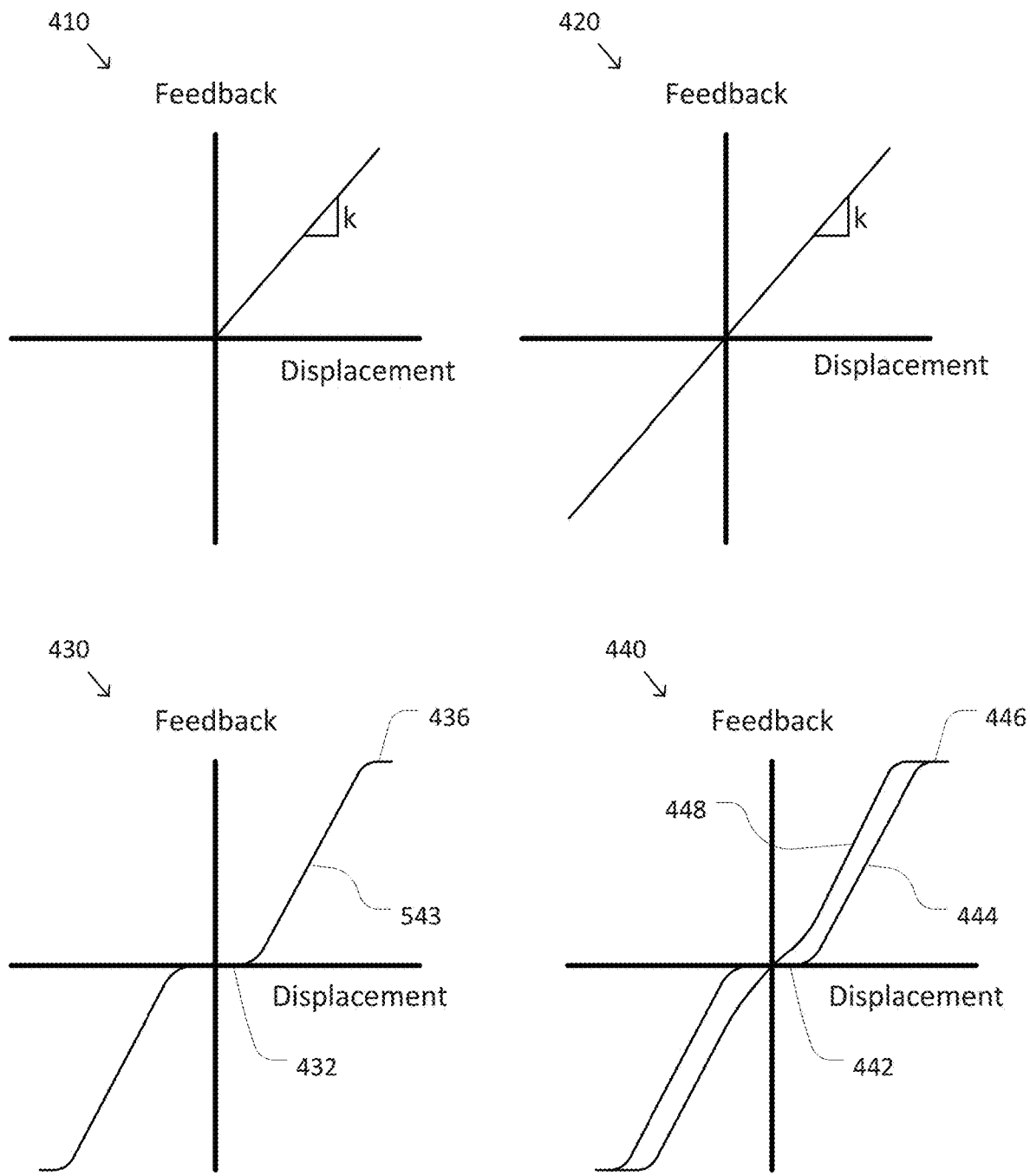
FIG. 4 is a simplified diagram of several example virtual feedback models according to some embodiments.

FIG. 4 is a simplified diagram of several example virtual feedback models according to some embodiments. Each of the virtual feedback models in FIG. 4 is representative of a potential feedback model that may be used with an input control that may be displaced and/or moved along a single axis in a manner consistent with the horizontal movement described with respect to input control 310 in FIG. 3. Each of the virtual feedback models are also based on an input control that may be displaced about the single axis of motion from a reference point. The virtual feedback models of FIG. 4 are shown in the form of a transfer function that describes the relationship between an amount of displacement as represented by the horizontal axis, with the crossing point at the vertical axis representing the reference point, and an amount of feedback as represented by the vertical axis. In some examples, the amount of feedback may correspond to or be proportional to an amount of force that may be applied to the input control by one or more haptic feedback actuators. As can be appreciated, any of the various parameters of the virtual feedback models may be changed at any time allowing an operator and/or another control system to change the pattern and/or amount of feedback applied to the input control. In some examples, this may include dynamically changing the reference point about which the displacement is determined (e.g., separating the reference point from the virtual anchor point and/or moving the virtual anchor point) and/or dynamically changing any of the slopes, setpoints, or even the virtual feedback model being used with a corresponding input control.

As one example, FIG. 4 depicts a unidirectional linear feedback model 410. As shown, unidirectional feedback model 410 generates feedback proportional to a positive displacement of an input control from a reference point and no feedback for a negative displacement. The amount of feedback is controlled by the slope k, with larger values of k providing higher force feedback for a given displacement and smaller values of k providing lower force feedback for the given displacement. In some examples, the role of positive and negative displacements may be reversed with feedback being generated for negative displacements and not for positive displacements. In some examples, unidirectional feedback model 410 may provide a suitable approximation of the force feedback that may be applied by a virtual spring that provides force feedback only when under tension.

FIG. 4 also depicts a bidirectional linear feedback model 420. As with unidirectional feedback model 410, bidirectional linear feedback model 420 provides an amount of feedback that is proportional to the amount of displacement with the scaling controlled by the slope k. Bidirectional linear feedback model 420, however, applies to both positive and negative displacements. Thus, bidirectional feedback model 420 may be used to provide feedback in a direction toward the reference point. In some examples, bidirectional feedback model 420 may provide a suitable approximation of the force feedback that may be applied by a virtual spring that provides force feedback during both tension and compression.

The virtual feedback models may be non-linear as well, such as is shown in a non-linear feedback model 430. Non-linear feedback model 430 includes three zones of general feedback operation. In a start-up zone 432, little or no feedback is applied until the displacement exceeds a start-up threshold. In some examples, start-up zone 432 may reduce undesirable vibrations in the input control due to the applied feedback and/or provide a start-up region with no feedback. In a primary operational zone 434, the amount of feedback may be approximately proportional to the amount of displacement. And, in a saturation zone 436, the amount of feedback provided may reach a pre-assigned maximum value. In some examples, the pre-assigned maximum value may be based on a maximum amount of feedback that may be supplied by the one or more haptic actuators, a physical strength of a user, and/or the like.

The virtual feedback models may also include hysteresis and/or hysteresis-like effects, as is shown in a hysteresis feedback model 440. Like non-linear feedback model 430, hysteresis feedback model 440 includes a start-up zone 442, a ramp-up operational zone 444, and a saturation zone 446. Hysteresis feedback model 440 further includes a ramp-down operational zone 448 that is different from ramp-up operational zone 444. In some examples, hysteresis feedback model 440 provides the advantages of non-linear feedback model 430, but may also provide a better return to reference point characteristic as feedback may be applied up to the point where the input control is returned to the reference point.

Although not shown in FIG. 4, other variations in the virtual feedback models are possible. According to some embodiments, the virtual feedback models may represent other physical components. In some examples, the horizontal axis may represent position and/or velocity rather than displacement. In some examples, the vertical axis may represent force, friction, and/or the like. According to some embodiments, more complex virtual feedback models may be used. In some examples, the virtual feedback model may approximate a piece-wise linear behavior. In some examples, other non-linear models may be used.

In some examples, the virtual feedback models may include two, three, or even more input dimensions with corresponding multiple displacement axes and/or a virtual feedback surface for each of the corresponding two, three, or more dimensional feedback axes. In some examples, each of the input dimensions and/or axes may correspond with a positional degree of freedom, a rotational degree of freedom, a physical direction, time, and/or the like. In some embodiments, the multi-dimensional feedback model may be isotropic and/or non-isotropic. In some examples, the virtual feedback model may emulate a non-isotropic virtual spring having different coefficients in different directions. In some examples, the virtual feedback model may emulate higher stiffness in one direction and lower stiffness in another direction. In some examples, the virtual feedback model may show linear behavior in one direction, and nonlinear direction in another direction. In general, it is not usually possible to implement this flexibility in feedback using physical feedback mechanisms, such as a series of spring, dampers, and/or the like.

According to some embodiments, the virtual feedback models may be asymmetric. In some examples, different slopes, non-linear patterns, hysteresis, and/or the like may be applied to the positive and negative displacements. For example, bidirectional linear feedback model 420 for negative displacements may be combined with hysteresis feedback model 440 for positive displacements. According to some embodiments, the virtual feedback models may provide feedback values that correspond to other behaviors associated with the corresponding input control. In some examples, virtual feedback model 430 may roughly approximate the same shape as a control model used to interpret the displacement of the input control for a control algorithm or model, so that small displacements of the input control result in zero input into the control algorithm and large displacements on the input control provide a saturated maximum input into the control algorithm.

In some embodiments, virtual feedback mechanism 320 may be easily adapted to handle displacements and/or movement along any degree of freedom in movement including positional and/or rotational displacements. In some examples, any measured displacement of input control 310 may be converted into components along any degree of freedom. In some examples, when input control 310 is displaced in both the horizontal and vertical directions, the components in the horizontal and vertical directions may be determined and then one or more virtual feedback models may be applied to the horizontal and vertical components. In some examples, this may include separate vertical and horizontal virtual feedback models so that it is possible to determine and apply different models of feedback to input control 310 in the horizontal and vertical directions.

Figure 5:
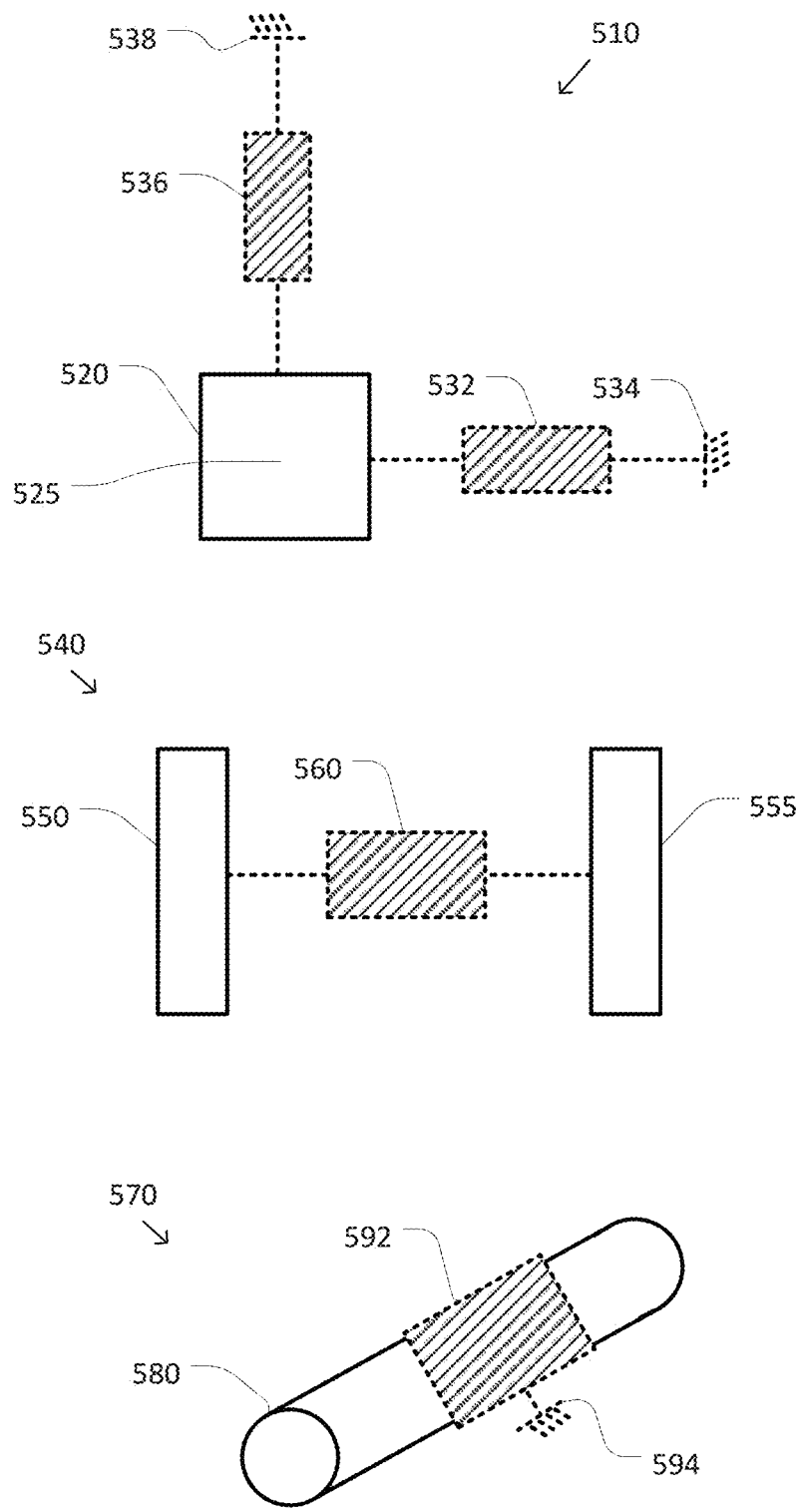
FIG. 5 is a simplified diagram of several example virtual feedback mechanism configurations according to some embodiments.

FIG. 5 is a simplified diagram of several example virtual feedback mechanism configurations according to some embodiments. Each of the configurations in FIG. 5 is representative of a potential configuration of one or more virtual feedback mechanisms with one or more input controls and demonstrates how the one or more virtual feedback mechanisms may provide feedback to the one or more input controls. As with the configuration of FIG. 3, any virtual feedback model, such as the virtual feedback models of FIG. 4 may be used for the virtual feedback mechanisms shown in FIG. 5.

A configuration 510 demonstrates how two or more virtual feedback mechanisms may be used with an input control 520. As shown, input control 520 is virtually coupled to a virtual feedback mechanism 532 anchored to a virtual anchor point 534 and a virtual feedback mechanism 536 anchored to a virtual anchor point 538. In some examples, virtual anchor points 534 and 538 may correspond to different locations and/or reference points. In some examples, virtual anchor points 534 and/or 538 may correspond to a reference point 525 located near a central position on input control 520. According to some embodiments, configuration 510 may be consistent with a joy-stick type input control similar to the one shown in FIGS. 1A and 1B, and/or may be consistent with articulated input control 200.

Use of both virtual feedback mechanisms 532 and 536 may simplify the feedback modeling for input control 520. In some examples, by using separate virtual feedback mechanisms 532 and 536, each of the virtual feedback mechanisms 532 and 536 may include simpler one-dimensional virtual feedback models. The virtual feedback model for virtual feedback mechanism 532 may provide feedback based on horizontal displacements of input control 520 and the virtual feedback model for virtual feedback mechanism 536 may provide feedback based on vertical displacements of input control 520. In some examples, the feedback from virtual feedback mechanism 532 may be used to generate feedback levels for the one or more haptic actuators of input control 520 that apply to horizontal movement and feedback from virtual feedback mechanism 536 may be used to generate feedback levels for the one or more haptic actuators of input control 520 that apply to vertical movement. In some examples, superposition or some other combining strategy may be used to generate a composite feedback amount from the virtual feedback models of both virtual feedback mechanisms 532 and 536. In some examples, when multiple virtual feedback mechanisms are virtually coupled to handle 230, the feedback levels and/or composite feedback may be used to apply feedback forces on handle 230 through the actuators associated with the joints 220.

A configuration 540 demonstrates the use of a virtual feedback mechanism 560 to induce compliant behavior between an input control 550 and an input control 555. By using a relative displacement between input controls 550 and 555, an amount of feedback may be generated to, for example, encourage operation so that input controls 550 and 555 may track each other. In some examples, this may support coordination between two separate operators, respectively operating input controls 550 and 555.

A configuration 570 demonstrates an example torsion-type virtual feedback mechanism for use with a rotatable input control 580. A virtual torsional feedback mechanism 592 may be virtually coupled to rotatable input control 580 and a virtual anchor point 594. The virtual feedback model of virtual torsional feedback mechanism 592 may emulate the behavior of a torsional spring. Thus, as rotatable input control 580 is rotated and generates an angular displacement, the angular displacement may be used to induce a torsional feedback in rotatable input control 580. In some examples, virtual torsional feedback mechanism 592 may be used to provide rotational feedback to an input control, such as to provide torsional feedback to roll, pitch, and/or yaw orientations in an articulated input control like articulated input control 200.

Although not shown in FIG. 5, other configurations of virtual feedback mechanisms are possible. According to some embodiments, more than two virtual feedback mechanisms may be used. In some examples, a third virtual feedback mechanism may be used to handle displacements in an up and down direction orthogonal to both the horizontal and the vertical. In some examples, a series of virtual feedback mechanisms may be virtually coupled radially about input control 520 so as to more uniformly direct input control 520 to a centrally located reference point. According to some embodiments, the combinations may be mixed and matched. In some examples, additional virtual feedback mechanisms may virtually couple additional input controls and/or virtual anchor points to either input control 550 and/or input control 555. Thus, a mesh of virtually coupled input controls may be created. According to some embodiments, different types of virtual feedback mechanisms may be combined. In some examples, a joy-stick type input control may be virtually coupled to horizontal and vertical virtual feedback mechanisms, such as those shown in configuration 510 and a torsional virtual feedback mechanism, such as virtual torsional feedback mechanism 592 in configuration 570. In this way feedback could be applied to the joy-stick type input control to support both horizontal and vertical displacements, but also for rotational displacements. In some examples, an articulated input control, such as articulated input control 200 may be virtually coupled to one or more virtual feedback mechanisms that provide feedback that push handle 230 toward a reference point and one or more virtual torsional feedback mechanisms to push handle 230 toward a reference orientation with roll, pitch, and/or yaw components.

Figure 6:
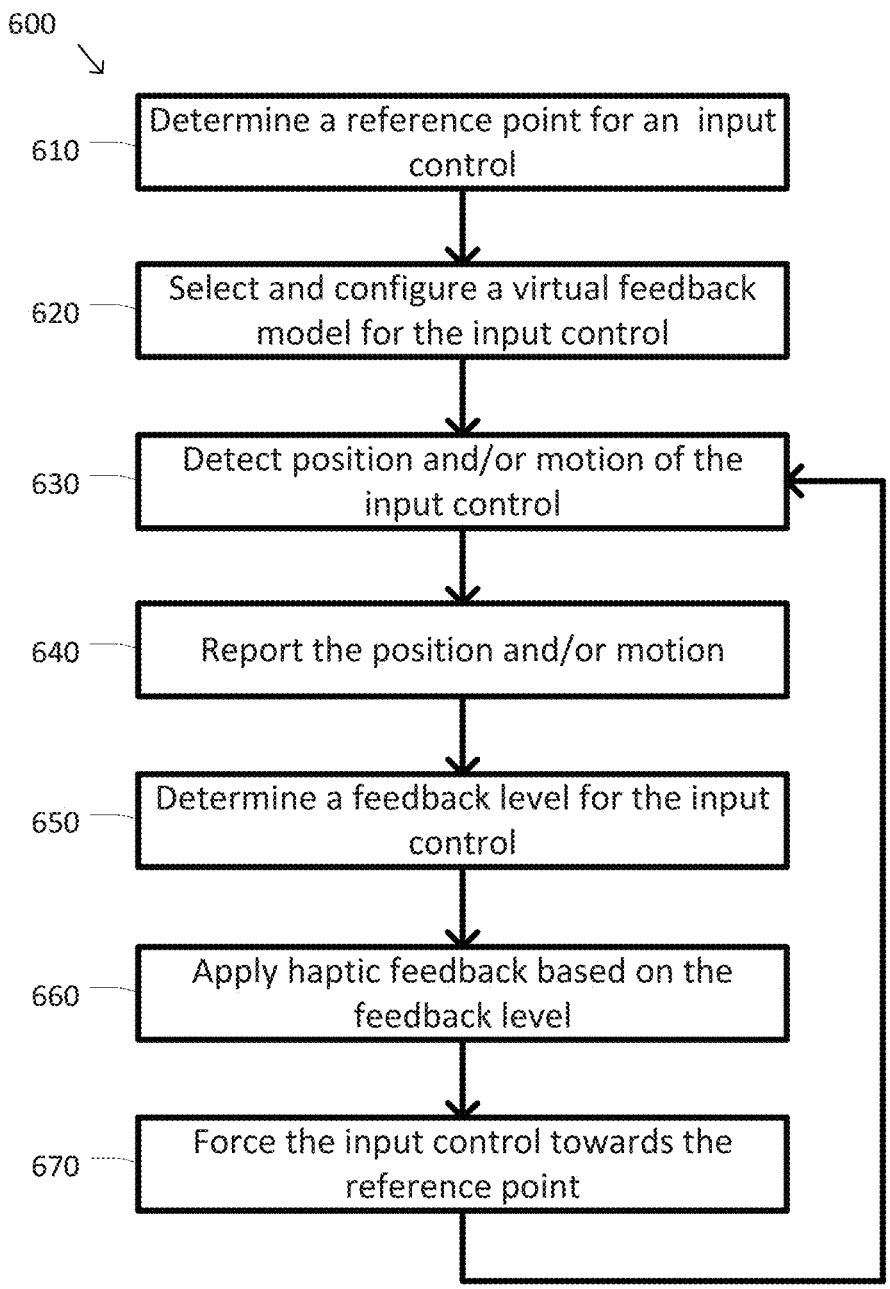
FIG. 6 is a simplified diagram of a method of generating feedback on an input control according to some embodiments.

FIG. 6 is a simplified diagram of a method 600 of generating feedback on an input control according to some embodiments. One or more of the processes 610-670 of method 600 may be implemented, at least in part, in the form of executable code stored on non-transient, tangible, machine readable media that when run by one or more processors, may cause the one or more processors to perform one or more of the processes 610-670. In some embodiments, the input control may be any of the input controls 200, 310, 520, 550, 555, and/or 580. In some embodiments, method 600 may be used to implement the equivalent of a dead-man's switch.

At a process 610, a reference point for an input control is determined. Before feedback may be applied to an input control, a reference point is generally determined for the input control. In most instances the reference point becomes a reference point about which displacements and/or motions are determined and may often be at a point where zero feedback is typically applied to the input control. In some embodiments, the reference point may be determined based on the physical geometry of the input control. In some examples, the reference point may be at one end or another of the range of motion of the input control and/or may be at any point along the range of motion, such as at a center point. In some examples, when the input control is an articulated input control, the reference point may correspond to a point within a console workspace. In some examples, where the input control has unrestricted motion, such as a rotational input control without stops, the reference point may be at any rotational angle of the rotational input control. In some examples, the reference point may be selectable based on a command received from another input device and/or from an operator. In some examples, the reference point may be determined based on the position of the input control when the command is received. In some examples, the position of the input control may be determined using one or more input/output (I/O) lines, buses, and/or network links coupled to the input control. In some examples, the input control may be any of the input controls 200, 310, 520, 550, 555, and/or 580.

At a process 620, a virtual feedback model for the input control is selected and configured. Depending on the feedback behavior desired for the input control, a virtual feedback model is selected and then configured. In some examples, this may include selecting any of the virtual feedback models described in FIG. 4 or some other suitable virtual feedback model. This may include selecting between unidirectional and bidirectional models, linear and non-linear models, isotropic and/or non-isotropic models, and/or models with or without hysteresis. The virtual feedback model may then be configured with appropriate slopes, break points, start-up thresholds, saturation values, and/or the like. In some examples, the virtual feedback model may be selected and/or configured by an operator using a catalog of one or more parameterized virtual feedback models.

At a process 630, a position and/or motion of the input control is detected. Positional and/or movement information for the input control is received from the input control. In some examples, the position and/or movement of the input control may be determined using the one or more I/O lines, buses, and/or network links coupled to the input control. In some examples, the position and/or motion may be received as one or more analog or digital values, one or more pulse counts or pulse widths, in one or more messages, in one or more network packets, and/or the like. In some examples, the position and/or input control may be determined from one or more joint angles, one or more joint positions, and/or one or more kinematic models of an articulated arm associated with the input control. In some examples, the kinematic models may be used to determine a position and/or an orientation of a handle or user grasp point in a console workspace based on the joint angles and/or positions. In some examples, the position and/or motion may be converted to a displacement from the reference point determined during process 610. In some examples, when the input control is being used to control an end effector, either remotely and/or via teleoperation, the displacement may correspond to a position and/or an orientation of the end effector relative to a reference point for the end effector.

At a process 640, the position and/or motion is reported. Because the input control is also likely providing a command and/or other input to a motion control and/or motion planning algorithm, the received position and/or motion are provided to the motion control and/or motion planning algorithm. In some examples, the position and/or motion may be subject to signal conditioning, scaling, shifting, and/or the like before it is reported to the motion control and/or motion planning algorithm. In some examples, the motion control and/or motion planning algorithm may be responsible for manipulating an end effector in response to changes in position and/or orientation of the input control.

At a process 650, a feedback level for the input control is determined. Using the position and/or motion detected during process 630 and the virtual feedback model selected and configured during process 620, a feedback level or amount for the input control is determined. In some examples, the displacement determined based on the position and/or movement is converted to a feedback force using the virtual feedback models like those discussed with respect to FIG. 4.

At a process 660, haptic feedback is applied based on the feedback level. Using the feedback level determined during process 650, one or more output signals and or commands are generated and sent to the one or more haptic actuators of the input control using the I/O lines, buses, and/or network links coupled to the input control. In some examples, the one or more output signals or commands may include one or more analog or digital values, one or more pulse counts or pulse widths, one or more messages, one or more network packets, and/or the like. In some examples, when the input control is an articulated input control, the feedback level may be converted to joint forces and/or torques using one or more inverse kinematic models and/or Jacobians for the articulated arm associated with the articulated input control.

At an optional process 670, the input control is forced towards the reference point. When a suitable virtual feedback model is being applied to the input control, the haptic feedback applied during process 660 may apply a force that directs the input control back towards the reference point. In some examples, the virtual feedback model may push the input control back to the reference point when no operator or other input is applied.

Processes 630-670 are then repeated as more positions and/or motions of the input control are detected, reported, and then used to determine and generate appropriate feedback using the one or more haptic actuators.

As discussed above and further emphasized here, FIG. 6 is merely an example which should not unduly limit the scope of the claims. One of ordinary skill in the art would recognize many variations, alternatives, and modifications. According to some embodiments, the input control may be subject to feedback from more than one virtual feedback mechanism. In some examples, the position and/or motion detected during process 630 may be used to generate feedback levels from multiple virtual feedback models that are then used to determine the amount of haptic feedback to apply. In some examples, superposition or other combining algorithm may be used to generate the composite feedback for the input control. According to some embodiments, processes 610 and/or 620 may be executed periodically during the performance of method 600. In some examples, input may be received from an operator and/or another system that may change the selection and/or configuration of the virtual feedback model being used. In some examples, process 610 may be used to change the reference point for the input control. In some examples, process 620 may be used to change the feedback model being applied to the detected positions and/or motions.

Figure 7:
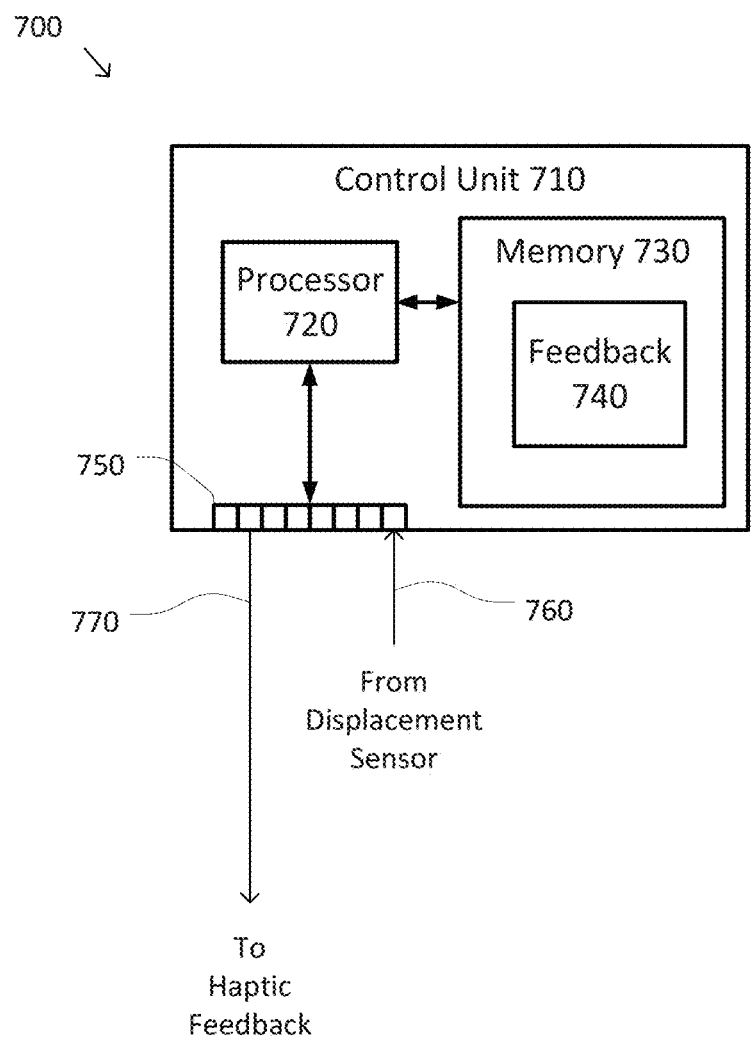
FIG. 7 is a simplified diagram of control system according to some embodiments.

FIG. 7 is a simplified diagram of control system 700 according to some embodiments. As shown in FIG. 7, control system 700 is based around a control unit 710. Control unit 710 may be part of a larger computer and/or electronic system (not shown) that may receive inputs from user controls, process those inputs, and implement one or more control algorithms based on those inputs. According to some embodiments, control system 700 may be used as part of and/or in conjunction with an operator workstation for a computer-assisted surgical device that corresponds to a da Vinci® Surgical System commercialized by Intuitive Surgical, Inc. of Sunnyvale, Calif. and/or a computer-assisted imaging device. The one or more control algorithms may use the inputs received from various input controls on the operator workstation to help control the position and movement of the computer-assisted surgical device and/or the computer-assisted imaging device. In some examples, these one or more control algorithms may account for kinematic models, support collision avoidance and/or coordinated motion, and/or the like.

Control unit 710 includes a processor 720 coupled to memory 730. Operation of control unit 710 is controlled by processor 720. And although control unit 710 is shown with only one processor 720, it is understood that processor 720 may be representative of one or more central processing units, multi-core processors, microprocessors, microcontrollers, digital signal processors, field programmable gate arrays (FPGAs), application specific integrated circuits (ASICs), and/or the like in control unit 710. Control unit 710 may be implemented as a stand-alone subsystem and/or board added to a computing device or as a virtual machine. In some embodiments, control unit may be included as part of the operator workstation and/or operated separately from, but in coordination with the operator workstation.

Memory 730 may be used to store software executed by control unit 710 and/or one or more data structures used during operation of control unit 710. Memory 730 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 730 includes an input control feedback application 740 that may be used to support the generation of feedback in various input controls coupled to control unit 710. Input control feedback application 740 may include one or more application programming interfaces (APIs) for implementing method 600, which includes one or more processes for receiving input control positions, displacements, and/or movement from one or more input devices, determining corresponding feedback values, and generating output signals for one or more haptic feedback actuators. And although input control feedback application 740 is depicted as a software application, input control feedback application 740 may be implemented using hardware, software, and/or a combination of hardware and software.

To support input control feedback application 740, control unit 710 additionally includes an interface 750 with one or more I/O ports. Interface 750 may be of any suitable type such as dedicated I/O lines, network links, inter-integrated circuit ($I^2C$) buses, serial peripheral interface (SPI) buses, parallel ports, analog I/O lines, and/or the like. Interface 750 may include one or more output lines, buses, and/or network links 760 for coupling control unit 710 to the one or more haptic actuators of an input control so that input control feedback application 740 may control feedback in the input control. Interface 750 may also include one or more input lines and/or buses 770 for coupling control unit 710 to one or more sensors of the input control so that input control feedback application 740 may receive position, displacement, and/or movement information of the input control. In some examples, the one or more output lines 760 may be coupled to inputs 350 of input control 310 and the one or more input lines, buses, and/or network links 770 may be coupled to outputs 340 of input control 310. In some examples, the one or more output lines 760 and the one or more input lines 770 may be combined in the same bi-directional lines, the same buses, and/or the same network links. In some examples, interface circuitry associated with the one or more interface 750 may include one or more bus controllers, I/O controllers, network interfaces, analog to digital convertors, digital to analog convertors, data acquisition systems, and/or the like.

Some examples of control units, such as the control unit 700 may include non-transient, tangible, machine readable media that include executable code that when run by one or more processors (e.g., processor 710) may cause the one or more processors to perform the processes of method 600. Some common forms of machine readable media that may include the processes of method 600 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although the illustrative embodiments described in FIGS. 3-7 are directed to input controls, such as haptic input controls, one of ordinary skill would understand that the virtual feedback mechanisms have broader applicability. According to some embodiments, any of the input controls may be replaced with any virtual or physical element in a system being controlled. Thus, for example, the example configuration 540 may be adapted to provide compliant motion between the end effectors of two devices with articulated arms where the virtual feedback model of virtual feedback mechanism 560 may be used to encourage a desired physical relationship between the two end effectors by basing the amount of feedback on the relative distances between the two end effectors.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A system comprising:
   a virtual feedback device virtually coupled between a first device and a second device; and
   a control unit comprising one or more processors;
   wherein the control unit is configured to:
   select a first virtual feedback model (VFM) for the virtual feedback device from among a plurality of VFMs for the virtual feedback device;
   configure the first VFM;
   determine, based on information received from one or more first sensors for detecting information related to a position of the first device and one or more second sensors for detecting information related to a position of the second device, a relative displacement between the first device and the second device;
   determine, based on the relative displacement and the first VFM, a feedback level;
   send one or more first feedback commands, based on the feedback level, to one or more first actuators for inducing feedback on the first device; and
   send one or more second feedback commands, based on the feedback level, to one or more second actuators for inducing feedback on the second device.

2. The system of claim 1, wherein the first VFM includes a transfer function that has one or more characteristics selected from a group consisting of unidirectional, bidirectional, linear, non-linear, asymmetric, symmetric, isotropic, non-isotropic, and hysteresis.

3. The system of claim 1, wherein the one or more first feedback commands and the one or more second feedback commands induce compliant motion between the first device and the second device.

4. The system of claim 1, wherein the control unit is further configured to:
   select a second VFM for the virtual feedback device from among the plurality of VFMs for the virtual feedback device;
   configure the second VFM; and
   determine the feedback level further based on the second VFM.

5. The system of claim 1, wherein the first VFM emulates one or more feedback devices selected from a group consisting of a mechanical spring, a damper, a dashpot, a shock absorber, a torsion spring, and a gas spring.

6. The system of claim 1, wherein the relative displacement is a linear displacement, an angular displacement, or both a linear displacement and an angular displacement.

7. The system of claim 1, wherein the first device is a haptic device, an operator control, or an end effector of an articulated device.

8. The system of claim 1, wherein the first VFM includes a transfer function that includes a region of zero feedback level.

9. The system of claim 1, wherein the first VFM includes a transfer function that includes a saturation region.

10. The system of claim 1, wherein:
    the control unit is further configured to change one or more parameters of the first VFM; and
    the one or more parameters correspond to one or more slopes, break points, start-up thresholds, or saturation values of a transfer function associated with the first VFM.

11. The system of claim 1, wherein the control unit is further configured to:
    select a second VFM for the virtual feedback device from among a plurality of VFMs for the virtual feedback device;
    configure the second VFM;
    determine, based on the relative displacement and the second VFM, a second feedback level;
    determine a third feedback level based on superposition of the feedback level and the second feedback level; and
    send the one or more first feedback commands, further based on the third feedback level, to the one or more first actuators; and
    send the one or more second feedback commands, further based on the third feedback level, to the one or more second actuators.

12. A method comprising:
    selecting, by a control unit, a first virtual feedback model (VFM) for a virtual feedback device from among a plurality of VFMs for the virtual feedback device;
    configuring, by the control unit, the first VFM;
    determining, by the control unit based on information received from one or more first sensors for detecting information related to a position of a first device and one or more second sensors for detecting information related to a position of a second device, a relative displacement between the first device and the second device;
    determining, by the control unit based on the relative displacement and the first VFM, a feedback level;
    sending, by the control unit, one or more first feedback commands, based on the feedback level, to one or more first actuators for inducing feedback on the first device; and
    sending, by the control unit, one or more second feedback commands, based on the feedback level, to one or more second actuators for inducing feedback on the second device.

13. The method of claim 12, wherein the one or more first feedback commands and the one or more second feedback commands induce compliant motion between the first device and the second device.

14. The method of claim 12, wherein the first VFM emulates one or more feedback devices selected from a group consisting of a mechanical spring, a damper, a dashpot, a shock absorber, a torsion spring, and a gas spring.

15. The method of claim 12, wherein the relative displacement is a linear displacement, an angular displacement, or both a linear displacement and an angular displacement.

16. The method of claim 12, wherein the first device is a haptic device, an operator control, or an end effector of an articulated device.

17. A non-transitory machine-readable medium comprising executable code, which when executed by a control unit cause the control unit to perform a method comprising:
   selecting a first virtual feedback model (VFM) for a virtual feedback device from among a plurality of VFMs for the virtual feedback device;
   configuring the first VFM;
   determining, based on information received from one or more first sensors for detecting information related to a position of a first device and one or more second sensors for detecting information related to a position of a second device, a relative displacement between the first device and the second device;
   determining, based on the relative displacement and the first VFM, a feedback level;
   sending one or more first feedback commands, based on the feedback level, to one or more first actuators for inducing feedback on the first device; and
   sending one or more second feedback commands, based on the feedback level, to one or more second actuators for inducing feedback on the second device.

18. The non-transitory machine-readable medium of claim 17, wherein the one or more first feedback commands and the one or more second feedback commands induce compliant motion between the first device and the second device.

19. The non-transitory machine-readable medium of claim 17, wherein the relative displacement is a linear displacement, an angular displacement, or both a linear displacement and an angular displacement.

20. The non-transitory machine-readable medium of claim 17, wherein the first device is a haptic device, an operator control, or an end effector of an articulated device.

* * * * *

UNITED STATES PATENT AND TRADEMARK OFFICE
CERTIFICATE OF CORRECTION

PATENT NO. : 10,729,506 B2
APPLICATION NO. : 16/261122
DATED : August 4, 2020
INVENTOR(S) : Mahdi Azizian Page 1 of 1

It is certified that error appears in the above-identified patent and that said Letters Patent is hereby corrected as shown below:

On the Title Page

(63) Related U.S. Application Data:
Please delete "Continuation of application No. 15/128,397, filed as application No. PCT/US2015/021662 on Mar. 20, 2015, now Pat. No. 10,251,719." and insert --Continuation of application No. 15/128,397, filed on Sep. 22, 2016, now Pat. No. 10,251,719, which is a 371 of application No. PCT/US2015/021662, filed on Mar. 20, 2015.--.

Signed and Sealed this
Twenty-ninth Day of September, 2020

Andrei Iancu
*Director of the United States Patent and Trademark Office*